(12) United States Patent
Kellerman et al.

(10) Patent No.: US 9,452,015 B2
(45) Date of Patent: Sep. 27, 2016

(54) INTRAVASCULAR ARTERIAL TO VENOUS ANASTOMOSIS AND TISSUE WELDING CATHETER

(75) Inventors: Brad M. Kellerman, Escondido, CA (US); David Trottingwolf Aldridge, Laguna Hills, CA (US); David K. Wrolstad, Yucaipa, CA (US); Mark A. Ritchart, Murrieta, CA (US); Jeffrey E. Hull, Midlothian, VA (US)

(73) Assignees: Avenu Medical, Inc., San Juan Capistrano, CA (US); Baja Research, LLC, San Clemente, CA (US)

( * ) Notice: Subject to any disclaimer, the term of this patent is extended or adjusted under 35 U.S.C. 154(b) by 1186 days.

(21) Appl. No.: 13/161,356

(22) Filed: Jun. 15, 2011

(65) Prior Publication Data

US 2011/0306959 A1   Dec. 15, 2011

Related U.S. Application Data (60) Provisional application No. 61/480,818, filed on Apr. 29, 2011, provisional application No. 61/354,903, filed on Jun. 15, 2010.

(51) Int. Cl.
  *A61B 17/11*   (2006.01)
  *A61B 18/08*   (2006.01)
  (Continued)

(52) U.S. Cl.
  CPC ............ *A61B 18/1492* (2013.01); *A61B 17/11* (2013.01); *A61B 17/320068* (2013.01); *A61B 18/082* (2013.01); *A61B 18/18* (2013.01); *A61B 18/24* (2013.01); *A61B 2017/1107* (2013.01); *A61B 2017/1139* (2013.01);
  (Continued)

(58) Field of Classification Search
  CPC .... A61B 18/04; A61B 18/08; A61B 18/082; A61B 18/12; A61B 18/14; A61B 2018/00345; A61B 2018/00404; A61B 2018/00428; A61B 2018/00601; A61B 2018/04; A61B 2018/08; A61B 2018/082; A61B 2018/14; A61B 2018/1405; A61B 2018/1412; A61B 2018/1422; A61B 17/11; A61B 18/1492; A61B 2018/00619; A61B 17/068; A61B 2017/07285; A61B 10/02
  See application file for complete search history.

(56) References Cited

U.S. PATENT DOCUMENTS 5,290,278 A   3/1994  Anderson
5,425,731 A   6/1995  Daniel et al.
(Continued)

OTHER PUBLICATIONS

International Search Report and Written Opinion dated Oct. 31, 2011 in PCT Application No. PCT/US2011/040567.
(Continued)

*Primary Examiner* — Jaymi Della
*Assistant Examiner* — Yasamin Ekrami
(74) *Attorney, Agent, or Firm* — Donald E. Stout; Stout, Uxa & Buyan, LLP (57) ABSTRACT

A device for creating an arteriovenous (AV) fistula comprises an elongate member, a distal member connected to the elongate member and movable relative to the elongate member, and a heating member disposed on at least one of the movable distal member and the elongate member. The distal member comprises structure for capturing tissue to be cut to create the fistula, and the heating member is adapted to cut through the tissue to create the fistula. The elongate member comprises an elongate outer tube. A shaft connects the distal member to the elongate member, and is extendable and retractable to extend and retract the distal member relative to the elongate member.

22 Claims, 9 Drawing Sheets

(51) Int. Cl.
*A61B 18/14* (2006.01)
*A61B 18/00* (2006.01)
*A61B 18/18* (2006.01)
*A61B 17/32* (2006.01)
*A61B 18/24* (2006.01)

(52) U.S. Cl.
CPC .............. *A61B 2018/00386* (2013.01); *A61B 2018/00422* (2013.01); *A61B 2018/00601* (2013.01); *A61B 2018/00619* (2013.01); *A61B 2018/00714* (2013.01); *A61B 2018/1475* (2013.01)

(56) References Cited

U.S. PATENT DOCUMENTS

| | | | |
|---|---|---|---|
| 5,531,677 A * | 7/1996 | Lundquist et al. | 604/22 |
| 5,578,030 A * | 11/1996 | Levin | A61B 10/0233 606/39 |
| 5,769,086 A * | 6/1998 | Ritchart et al. | 600/566 |
| 5,830,222 A | 11/1998 | Makower | |
| 5,830,224 A | 11/1998 | Cohn et al. | |
| 5,893,369 A * | 4/1999 | LeMole | A61B 17/11 606/184 |
| 6,068,637 A | 5/2000 | Popov et al. | |
| 6,068,638 A | 5/2000 | Makower | |
| 6,071,292 A | 6/2000 | Makower et al. | |
| 6,083,223 A | 7/2000 | Baker | |
| 6,099,542 A | 8/2000 | Cohn et al. | |
| 6,190,353 B1 | 2/2001 | Makower et al. | |
| 6,235,027 B1 | 5/2001 | Herzon | |
| 6,283,983 B1 | 9/2001 | Makower et al. | |
| 6,302,875 B1 | 10/2001 | Makower et al. | |
| 6,330,884 B1 | 12/2001 | Kim | |
| 6,352,535 B1 * | 3/2002 | Lewis et al. | 606/45 |
| 6,375,615 B1 | 4/2002 | Flaherty et al. | |
| 6,379,319 B1 | 4/2002 | Garibotto et al. | |
| 6,398,797 B2 | 6/2002 | Bombard et al. | |
| 6,409,721 B1 | 6/2002 | Wheelock et al. | |
| 6,464,665 B1 | 10/2002 | Heuser | |
| 6,524,308 B1 * | 2/2003 | Muller et al. | 606/49 |
| 6,533,778 B2 | 3/2003 | Herzon | |
| 6,544,230 B1 | 4/2003 | Flaherty et al. | |
| 6,561,998 B1 | 5/2003 | Roth et al. | |
| 6,579,311 B1 | 6/2003 | Makower | |
| 6,613,081 B2 | 9/2003 | Kim et al. | |
| 6,616,675 B1 | 9/2003 | Evard et al. | |
| 6,669,709 B1 | 12/2003 | Cohn et al. | |
| 6,699,245 B2 | 3/2004 | Dinger et al. | |
| 6,709,444 B1 | 3/2004 | Makower | |
| 6,726,677 B1 | 4/2004 | Flaherty et al. | |
| 6,863,684 B2 | 3/2005 | Kim et al. | |
| 6,908,463 B2 | 6/2005 | Treat et al. | |
| 6,929,009 B2 | 8/2005 | Makower et al. | |
| 7,056,325 B1 | 6/2006 | Makower et al. | |
| 7,074,220 B2 | 7/2006 | Hill et al. | |
| 7,159,592 B1 | 1/2007 | Makower et al. | |
| 7,191,015 B2 | 3/2007 | Lamson et al. | |
| 7,316,655 B2 | 1/2008 | Garibotto et al. | |
| 7,351,247 B2 | 4/2008 | Kupiecki et al. | |
| 7,387,636 B2 | 6/2008 | Cohn et al. | |
| 7,588,566 B2 * | 9/2009 | Treat | A61B 18/085 606/29 |
| 7,729,738 B2 | 6/2010 | Flaherty et al. | |
| 7,846,172 B2 | 12/2010 | Makower | |
| 2001/0034518 A1 | 10/2001 | Edwards et al. | |
| 2002/0188294 A1 | 12/2002 | Couture et al. | |
| 2004/0073238 A1 * | 4/2004 | Makower | A61B 1/3137 606/153 |
| 2004/0082945 A1 * | 4/2004 | Clague | A61B 18/14 606/32 |
| 2005/0033330 A1 | 2/2005 | Vargas et al. | |
| 2005/0038457 A1 | 2/2005 | Vargas et al. | |
| 2005/0216042 A1 | 9/2005 | Gertner | |
| 2006/0009759 A1 * | 1/2006 | Chrisitian et al. | 606/41 |
| 2006/0030849 A1 * | 2/2006 | Mirizzi et al. | 606/50 |
| 2006/0111704 A1 * | 5/2006 | Brenneman | A61B 17/11 606/41 |
| 2006/0142788 A1 | 6/2006 | Wilson et al. | |
| 2006/0189979 A1 * | 8/2006 | Esch | A61B 18/1477 606/49 |
| 2006/0217697 A1 | 9/2006 | Lau et al. | |
| 2006/0217706 A1 * | 9/2006 | Lau | A61B 17/29 606/45 |
| 2007/0175963 A1 | 8/2007 | Bilotti et al. | |
| 2007/0208330 A1 * | 9/2007 | Treat | A61B 18/085 606/30 |
| 2009/0048589 A1 | 2/2009 | Takashino et al. | |
| 2009/0270882 A1 * | 10/2009 | O'Neill | 606/131 |
| 2010/0023132 A1 * | 1/2010 | Imran | 623/23.72 |
| 2010/0145331 A1 * | 6/2010 | Christian et al. | 606/33 |
| 2010/0152723 A1 | 6/2010 | Esch et al. | |
| 2011/0095067 A1 | 4/2011 | Ohdaira | |
| 2011/0251608 A1 | 10/2011 | Timm et al. | |
| 2011/0251609 A1 | 10/2011 | Johnson et al. | |
| 2011/0288546 A1 | 11/2011 | Abbott et al. | |
| 2012/0078246 A1 | 3/2012 | Mirizzi et al. | |
| 2012/0302935 A1 | 11/2012 | Miller et al. | |
| 2012/0316550 A1 | 12/2012 | Lau et al. | |

OTHER PUBLICATIONS

Office Action for U.S. Appl. No. 13/763,501, mailed on Feb. 29, 2016.

Office Action for U.S. Appl. No. 14/080,702, mailed on Mar. 10, 2016.

Office Action for U.S. Appl. No. 13/161,182, mailed on Mar. 25, 2016.

* cited by examiner

INTRAVASCULAR ARTERIAL TO VENOUS ANASTOMOSIS AND TISSUE WELDING CATHETER

This application claims the benefit under 35 U.S.C. 119(e) of the filing date of Provisional U.S. Application Ser. No. 61/354,903, entitled Systems and Methods for Creating Arteriovenous Fistulas, filed on Jun. 15, 2010, and Provisional U.S. Application Ser. No. 61/480,818, entitled Intravascular Arterial to Venous Anastomosis and Tissue Welding Catheter, filed on Apr. 29, 2011. Both applications are expressly incorporated herein by reference, in their entirety.

BACKGROUND OF THE INVENTION

In the body, various fluids are transported through conduits throughout the organism to perform various essential functions. Blood vessels, arteries, veins, and capillaries carry blood throughout the body, carrying nutrients and waste products to different organs and tissues for processing. Bile ducts carry bile from the liver to the duodenum. Ureters carry urine from the kidneys to the bladder. The intestines carry nutrients and waste products from the mouth to the anus.

In medical practice, there is often a need to connect conduits to one another or to a replacement conduit to treat disease or dysfunction of the existing conduits. The connection created between conduits is called an anastomosis.

In blood vessels, anastomoses are made between veins and arteries, arteries and arteries, or veins and veins. The purpose of these connections is to create either a high flow connection, or fistula, between an artery and a vein, or to carry blood around an obstruction in a replacement conduit, or bypass. The conduit for a bypass is a vein, artery, or prosthetic graft.

An anastomosis is created during surgery by bringing two vessels or a conduit into direct contact. The vessels are joined together with suture or clips. The anastomosis can be end-to-end, end-to-side, or side-to-side. In blood vessels, the anastomosis is elliptical in shape and is most commonly sewn by hand with a continuous suture. Other methods for anastomosis creation have been used including carbon dioxide laser, and a number of methods using various connecting prosthesis, clips, and stents.

An arterio-venous fistula (AVF) is created by connecting an artery to a vein. This type of connection is used for hemodialysis, to increase exercise tolerance, to keep an artery or vein open, or to provide reliable access for chemotherapy.

An alternative is to connect a prosthetic graft from an artery to a vein for the same purpose of creating a high flow connection between artery and vein. This is called an arterio-venous graft, and requires two anastomoses. One is between artery and graft, and the second is between graft and vein.

A bypass is similar to an arteriovenous graft. To bypass an obstruction, two anastomoses and a conduit are required. A proximal anastomosis is created from a blood vessel to a conduit. The conduit extends around the obstruction, and a second distal anastomosis is created between the conduit and vessel beyond the obstruction.

As noted above, in current medical practice, it is desirable to connect arteries to veins to create a fistula for the purpose of hemodialysis. The process of hemodialysis requires the removal of blood from the body at a rapid rate, passing the blood through a dialysis machine, and returning the blood to the body. The access to the blood circulation is achieved with catheters placed in large veins, prosthetic grafts attached to an artery and a vein, or a fistula where an artery is attached directly to the vein.

Fistulas for hemodialysis are required by patients with kidney failure. The fistula provides a high flow of blood that can be withdrawn from the body into a dialysis machine to remove waste products and then returned to the body. The blood is withdrawn through a large access needle near the artery and returned to the fistula through a second large return needle. These fistulas are typically created in the forearm, upper arm, less frequently in the thigh, and in rare cases, elsewhere in the body. It is important that the fistula be able to achieve a flow rate of 500 ml per minute or greater. Dialysis fistulas have to be close to the skin (<6 mm), and large enough (>4 mm) to access with a large needle. The fistula needs to be long enough (>6 cm) to allow adequate separation of the access and return needle to prevent recirculation of dialysed and non-dialysed blood between the needles inserted in the fistula.

Fistulas are created in anesthetized patients by carefully dissecting an artery and vein from their surrounding tissue, and sewing the vessels together with fine suture or clips. The connection thus created is an anastomosis. It is highly desirable to be able to make the anastomosis quickly, reliably, with less dissection, and with less pain. It is important that the anastomosis is the correct size, is smooth, and that the artery and vein are not twisted.

SUMMARY OF THE INVENTION

The present disclosed invention eliminates the above described open procedures, reduces operating time, and allows for a consistent and repeatable fistula creation.

It is well known that heat, whether its source is Radio Frequency (RF), resistance, or laser, will attach and weld tissue or vessels upon direct pressure and contact over the targeted weld area. This is often done with jaw-type, compression heat delivery devices. It is also well known that radially expandable devices such as balloons, metal cages, and baskets are often coupled with energy in the form of RF, or in the case of balloons, heated saline, and used intraluminally to ablate tissue, stop bleeding, or create a stricture.

The present invention uses catheter based devices that are advanced from one vessel into an adjacent vessel (i.e. a vein into an artery), join the vessel walls by applying heat, and cut through the two walls, creating an anastomosis.

The inventive catheter-based devices track over a guidewire which has been placed from a first vessel, such as a vein, into a second vessel, such as an artery, or more broadly between any other two vascular structures. The distal tip of the catheter has a dilating tip which allows the catheter to advance easily through the vessel walls. Proximal to the distal tip, the catheter has a significant reduction in diameter, and then a blunt, oval shaped tapered surface. As the catheter is tracked over the guidewire, the tapered distal tip easily passes into the adjacent vessel. As the catheter is further advanced, the blunt proximal surface comes into contact with the wall of the first vessel and encounters resistance, and cannot perforate through the wall into the second vessel. The distal tip, which has a matching blunt surface on its proximal end, is then retracted, capturing the walls of the two vessels between the two blunt surfaces. A known, controlled pressure (approximately 100 mN/mm$^2$-300 mN/mm$^2$) is applied between the two surfaces. The pressure can be controlled either internally in the catheter or by the handle attached to the proximal end of the catheter. Heat is then applied to the blunt surfaces to weld the walls of the two vessels together. It is possible to only apply the heat to one surface as well. Heat can be applied through several different methods, including, but not limited to, radiofrequency, resistance, inductance, or a combination thereof. The heat is controlled at a known temperature ranging from between about 100-150 C. The heat may be applied by either applying a steady heat, pulsing heat, or a combination thereof.

After coaptation of the vessel walls, the heat is then increased to cut through the vessel walls to create the desired size fistula. It should be noted that it is also possible to apply the same heat to both weld the vessel walls and to cut through the vessel.

More particularly, there is provided a device for creating an arteriovenous (AV) fistula, which comprises an elongate member, a distal member connected to the elongate member and movable relative to the elongate member, and a heating member disposed on at least one of the movable distal member and the elongate member. The distal member comprises structure for capturing tissue to be cut to create the fistula, and the heating member is adapted to cut through the tissue to create the fistula. The elongate member comprises an elongate outer tube.

A shaft connects the distal member to the elongate member, and is extendable and retractable to extend and retract the distal member relative to the elongate member. Preferably, the elongate member comprises a distal tapered face and the distal member comprises a proximal tapered face, wherein the distal tapered face and the proximal tapered face are substantially aligned to one another. In some embodiments, the heating member is disposed on the proximal tapered face, while in other embodiments, the heating member is disposed on the distal tapered face. Some embodiments further comprise a second heating member disposed on the distal tapered face. At least one of the heating member and the second heating member comprises an energized heater and a heat spreader disposed beneath the energized heater to spread heat away from the heater and create a temperature gradient. The heat spreader comprises heat conductive material, and is disposed on the tapered face beneath the heating member.

Preferably, the distal member is tapered and flexible, so that it can push through a small aperture between the two vessels to be joined with a fistula. In some embodiments, the distal member comprises a toggle member which is pivotal relative to the elongate member. In certain embodiments, a shaft is provided for connecting the toggle member to the elongate member, the shaft being extendable and retractable to extend and retract the toggle member relative to the elongate member, wherein the toggle member is pivotally connected to the shaft.

In one disclosed embodiment, the distal member comprises a flexible clamp to which is connected a heater, wherein the clamp is movable relative to the elongate member and is adapted to capture tissue to be cut to create the fistula. In this embodiment, the distal member further comprises a distal portion connected to a distal end of the elongate member, the distal portion having a side port therein through which the flexible clamp and connected heater extend.

A tissue receiving cavity may be associated with the heating member, to capture cut tissue. As noted above, in some embodiments, the heating member comprises an energized heater and a heat spreader disposed beneath the energized heater to spread heat away from the heater and create a temperature gradient. The heat spreader comprises heat conductive material.

In another aspect of the invention, there is disclosed a method of creating an AV fistula between adjacent first and second vessels, which comprises a step of inserting a guidewire from the first vessel into the second vessel, inserting a catheter comprising a proximal elongate member and a distal member over the guidewire, so that a tapered distal tip of the distal member comes into contact with a selected anastomosis site, and advancing the distal member into the second vessel, while the elongate member remains in the first vessel, thereby enlarging an aperture between the two vessels. A further step involves retracting the distal member toward the elongate member to clamp tissue surrounding the aperture between opposed surfaces on each of the distal member and the elongate member, and applying energy to a heating member on one of the distal member and the elongate member to cut and form the aperture, and to weld the edges thereof in order to create a desired fistula between the two vessels.

Preferably, the opposed surfaces on each of the distal member and the elongate member comprise aligned tapered faces, between which the tissue is clamped, wherein a heating member is disposed on at least one of the two aligned tapered faces. The method may advantageously further comprise a step of capturing cut tissue within a cavity disposed adjacent to the heating member. Heat may be dispersed away from the heating member using a heat spreader comprising a conductive material disposed on the tapered face beneath the heating member.

The invention, together with additional features and advantages thereof, may best be understood by reference to the following description taken in conjunction with the accompanying illustrative drawings.

DESCRIPTION OF THE PREFERRED EMBODIMENT

Figures 1, 12:
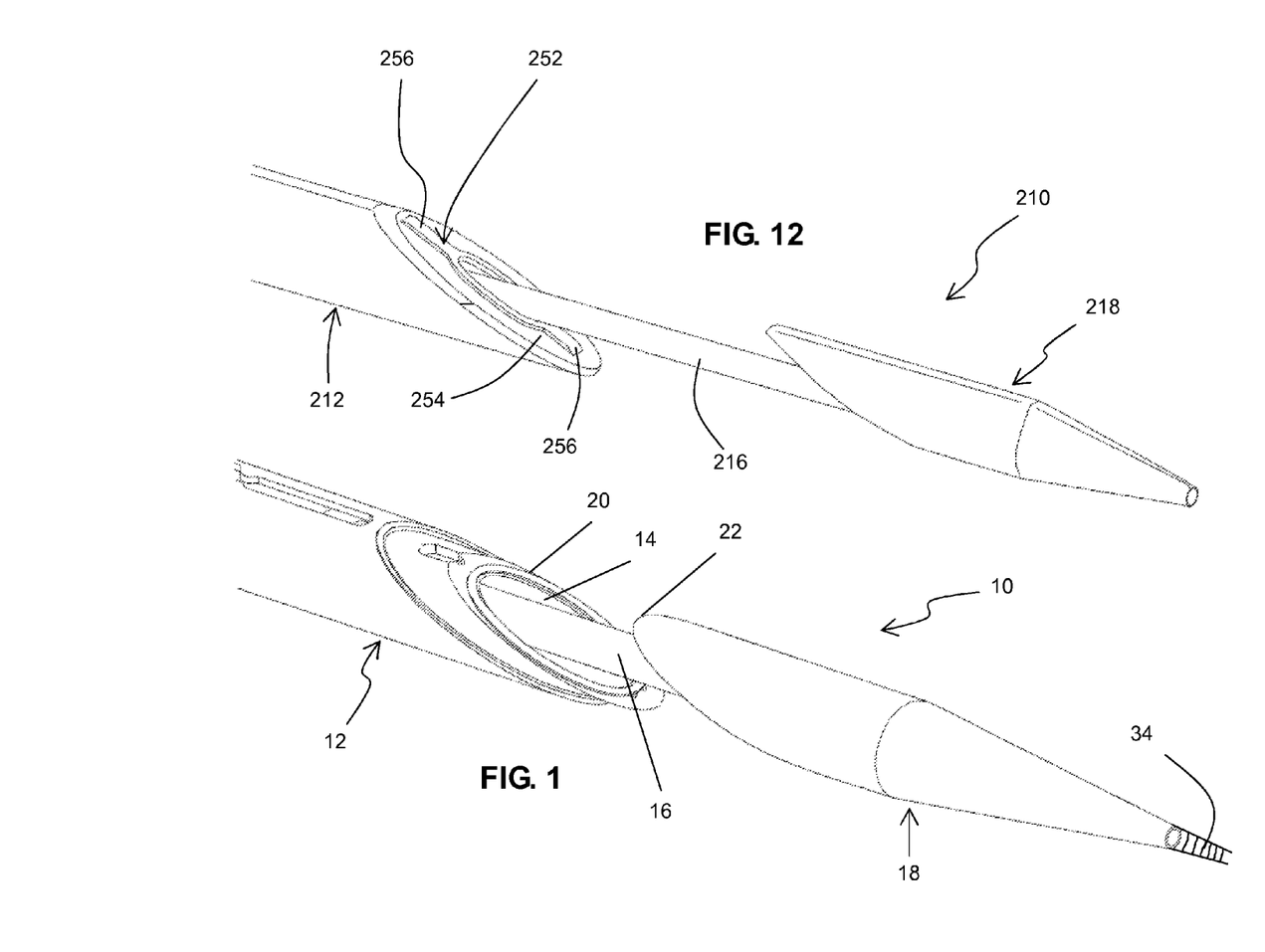
FIG. 1 is an isometric view of an embodiment of a catheter device constructed in accordance with the principles of the present invention.
FIG. 12 is an isometric view of yet another alternative embodiment of the present invention.

Referring now particularly to the drawings, there is shown in FIG. 1 a bi-polar tapered tip catheter embodiment 10, which comprises an elongate outer tube 12 having an outer diameter that can range from 3F-12F. It may be manufactured from a variety of materials, either polymer or metallic. It comprises a central lumen or opening 14, within which a tubular structure 16 for attaching a tip 18 may slide. There are separate lumina that run down the elongated core of the outer tube 12 for wiring to power electrodes or heating elements 20, 22 (proximal and distal, respectively), disposed on aligned tapered faces of the respective elongate outer tube 12 and distal tip 18, and to also measure the temperature during the coaptation and cutting processes. In this configuration, the catheter is powered using bipolar energy to the distal RF electrode 22 and the proximal RF electrode 20. The system can also be used in a monopolar configuration by grounding the patient and applying energy to one or both of the RF electrodes to increase the length of the coaptation. The RF electrodes cut at matching angles to increase the surface area of the coaptation and fistula size relative to the catheter diameter. These angles can be adjusted to achieve the desired fistula sizing. The RF electrodes are only electrically conductive on the front faces to maximize energy density. The electrodes are oval-shaped, and are adapted to cut an anastomosis which is larger than the diameter of the shaft 16.

The apparatus shown and described above in connection with FIG. 1 will now be further described in conjunction with an explanation of a particular method by which the system 10 may be used to create an AV fistula. This method is illustrated more particularly in FIGS. 2-9.

Figure 2:
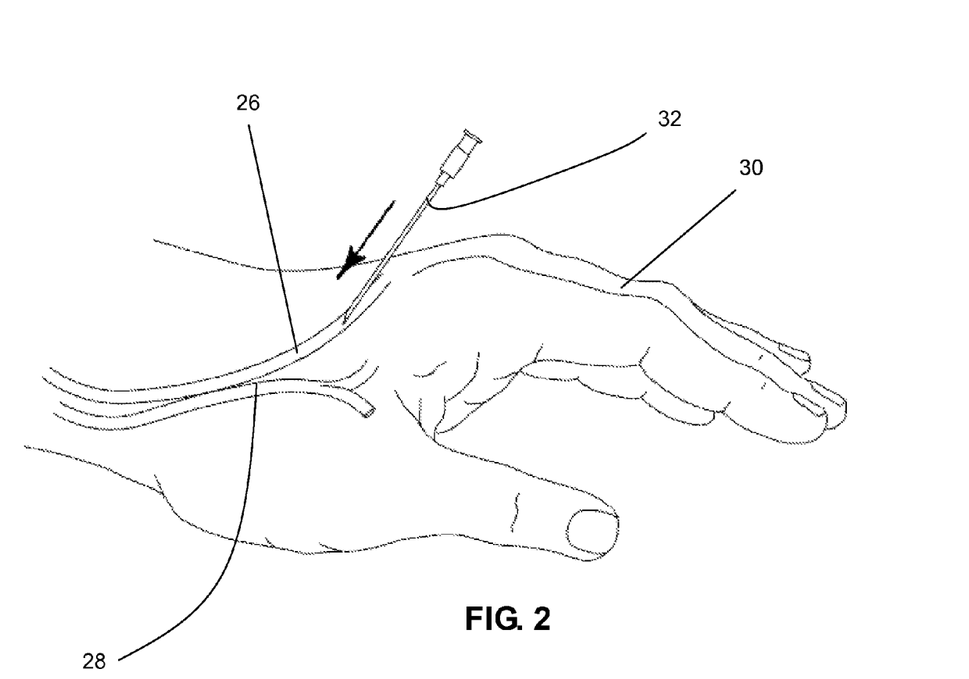
FIGS. 2-8 are schematic sequential views illustrating a method for creating a fistula performed in accordance with the principles of the present invention, and using an apparatus like that illustrated in FIG. 1 and disclosed herein.
Figure 3:
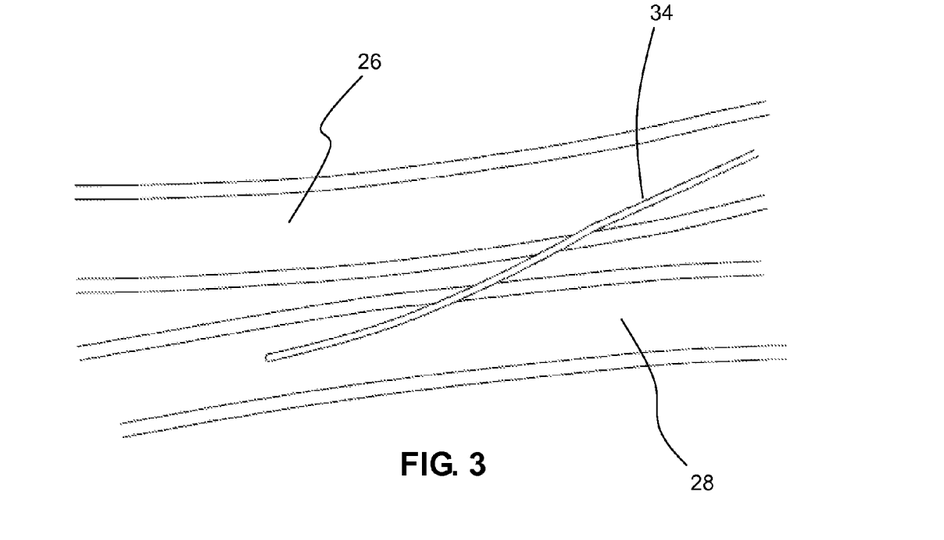

To begin the inventive method of creating an AV fistula, the practitioner selects an appropriate procedural site having each of a first vessel 26 and a second vessel 28 in close proximity to one another. In currently preferred approaches, the first vessel 26 comprises a vein, and the second vessel 28 comprises an artery, but the invention is not necessarily limited to this arrangement. As illustrated in FIG. 2, one presently preferred location is the hand 30 of a patient. Then, generally employing principles of the Seldinger technique, as shown in FIG. 2, the first vessel 26 is punctured by a needle 32, which is inserted therein, for the purpose of introducing an access sheath into the site. Then, using suitable techniques, such as the technique described in Provisional U.S. Application Ser. No. 61/354,903, filed on Jun. 15, 2010 and herein expressly incorporated by reference, in its entirety, a guidewire 34 is inserted into the patient, from the first vessel 26 into the second vessel 28, as shown in FIG. 3.

Figure 4:
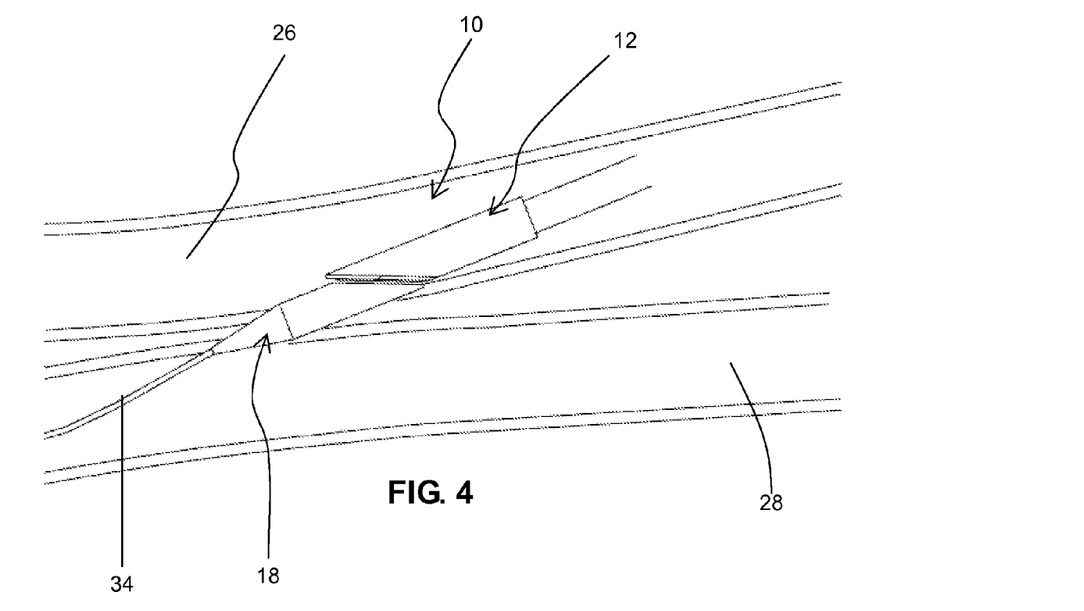
Figure 5:
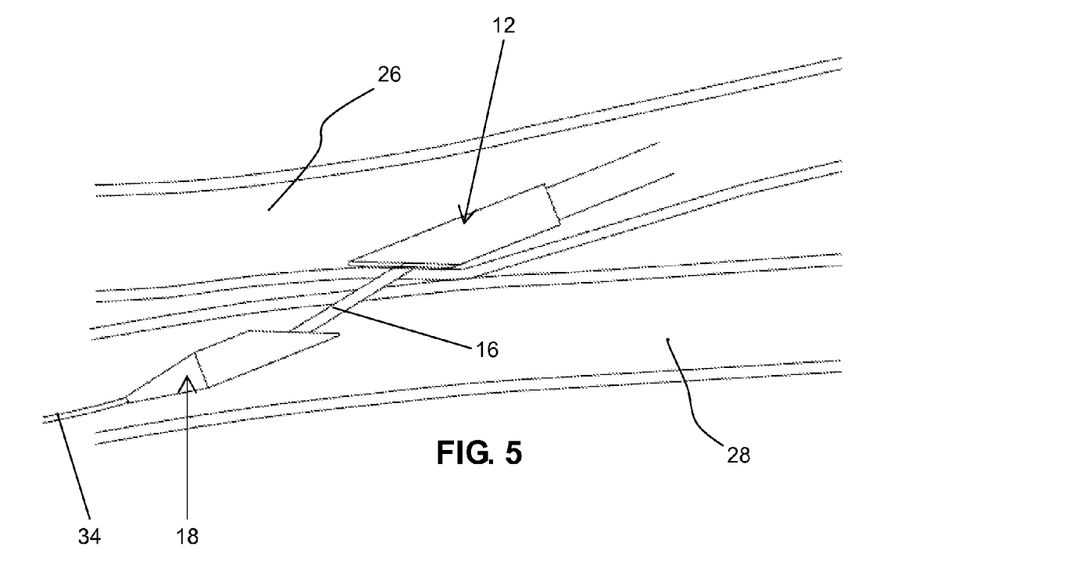

The guidewire 34 creates an access path for the catheter 10. The catheter 10 is inserted into the patient by loading a proximal end of the guidewire 34 into the tip 18, which is fabricated to be flexible and tapered. The catheter 10 is advanced further into the patient, tracking over the guidewire 34, until the tapered dilating distal tip 18 comes into contact with the selected anastomosis site. The device 10 can be tracked over the guidewire with the distal tip extended (as shown in FIG. 5) or retracted (as shown in FIG. 4). The distal tip 18 is extended and further advanced into the second vessel 28 (FIG. 5) by advancing the central tubular structure 16 distally from the outer tube 12, thereby dilating the fistula, so that the distal tip 18 is in the second vessel 28, and the tube 12 is in the first vessel 26, with its distal tapered surface contacting the inner wall of the first vessel 26. If resistance is felt, the entire system can be rotated to reduce the friction. At this juncture, the opening formed in the wall of the second vessel 28 has recovered back to a small diameter, and fits tightly around the shaft 16, as shown.

Figure 6:
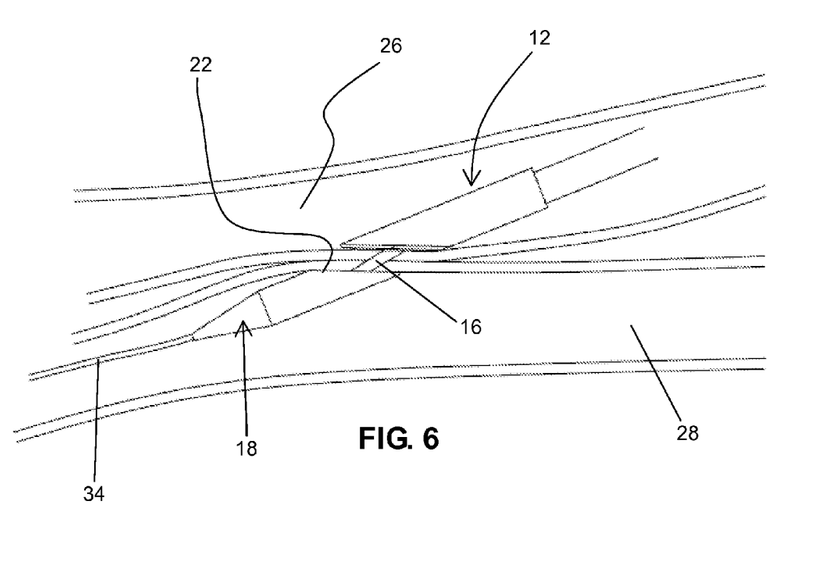

After the distal tip 18 is advanced into the second vessel 28, as illustrated in FIG. 6, a slight tension is applied to the distal RF electrode 22 to seat it against the vessel wall. The blunt shape of the proximal end of the distal tip 18 prevents the distal tip from pulling back through the vessel wall. The proximal end of the device 10, namely the outer tube 12, is then advanced to close the spacing between the tube 12 and tip 18, until the walls of the first and second vessels 26, 28, respectively, are captured between the facing blunt surfaces of each of the outer tube 12 and distal tip 18.

Figure 7:
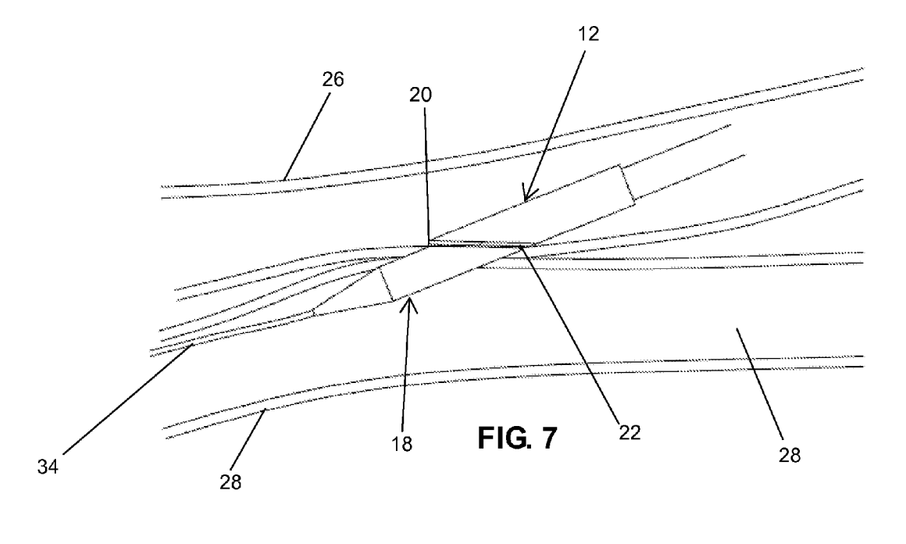
Figure 8:
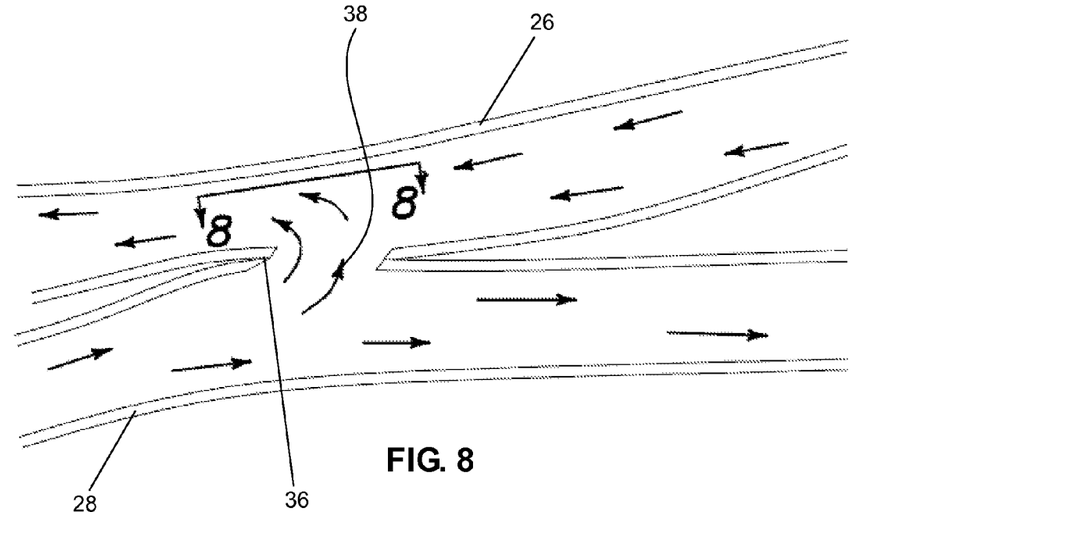

A controlled tension is maintained between the distal tip 18 and proximal outer tube 12, and at this juncture, with the vessel walls securely clamped, energy is applied to the RF electrodes 20, 22 (FIG. 7). As the electrodes weld and cut the vessels, the electrodes will move closer to one another. When fully retracted, the system 10 is designed so that the two electrodes 20, 22 cannot come into direct contact with one another, thus preventing the electrodes from shorting. A variety of RF energy profiles may be applied to achieve the desired coaptation and cutting. For example, during the coaptation phase, a tapered sine wave may be applied to maximize coagulation without cutting through the tissue. The energy may also be adjusted based upon the impedance of the tissue. Different pulse widths or duty cycles may be used to minimize the heat transferring into adjacent tissues. The hot wire is an oval shape and cuts an anastomosis larger than the diameter of the shaft 16. Within the oval shape of the cutting elements, there is a cavity for capturing the tissue that has been cut. The outer sliding tube is usable to push the tissue off the heater in case there is a sticking problem due to the heat.

Figure 9:
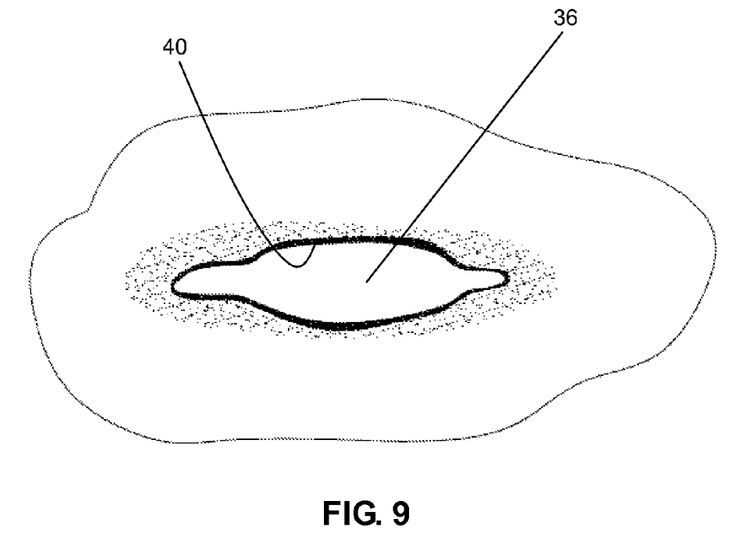
FIG. 9 is a schematic view illustrating an elongate aperture formed between two adjacent vessels to create the fistula, particularly highlighting the welded edges of the aperture.

Regarding the tissue welding process, more particularly, the RF energy functions to burn and fuse or weld the vessels together, creating an elongate aperture 36 (FIG. 8) through the opposing walls of each of the first and second vessels, as well as any intervening tissue. As formed, the elongate aperture 36 will typically resemble a slit. However, as pressurized flow 38 begins to occur through the slit or aperture 36, which creates a communicating passage between the first vessel and the second vessel, the aperture widens responsive to the pressure, taking the shape of an ellipse as it opens to form the desired fistula. This effect is illustrated in FIG. 9. The edges 40 of the aperture are cauterized and welded. FIG. 9 illustrates the weld from the venous (first vessel) side. As shown, the cut area corresponds to the shape of the heater wire. It can be of multiple shapes, such as round, oval, a slit, or a combination as shown. The area outside of the cut has been welded due to the flat face of the catheter in the vein (first vessel) being larger than the cutting wire. The heat from the wire is also preferably spread over this area by a conductive material that is below the heater, as will be described below. This creates a temperature gradient, which is a particularly advantageous feature of the present invention.

Tissue welding of the type intended to occur in the practice of these inventive methods is discussed in U.S. Pat. No. 6,908,463, to Treat et al., which is herein expressly incorporated by reference, in its entirety.

Figure 10:
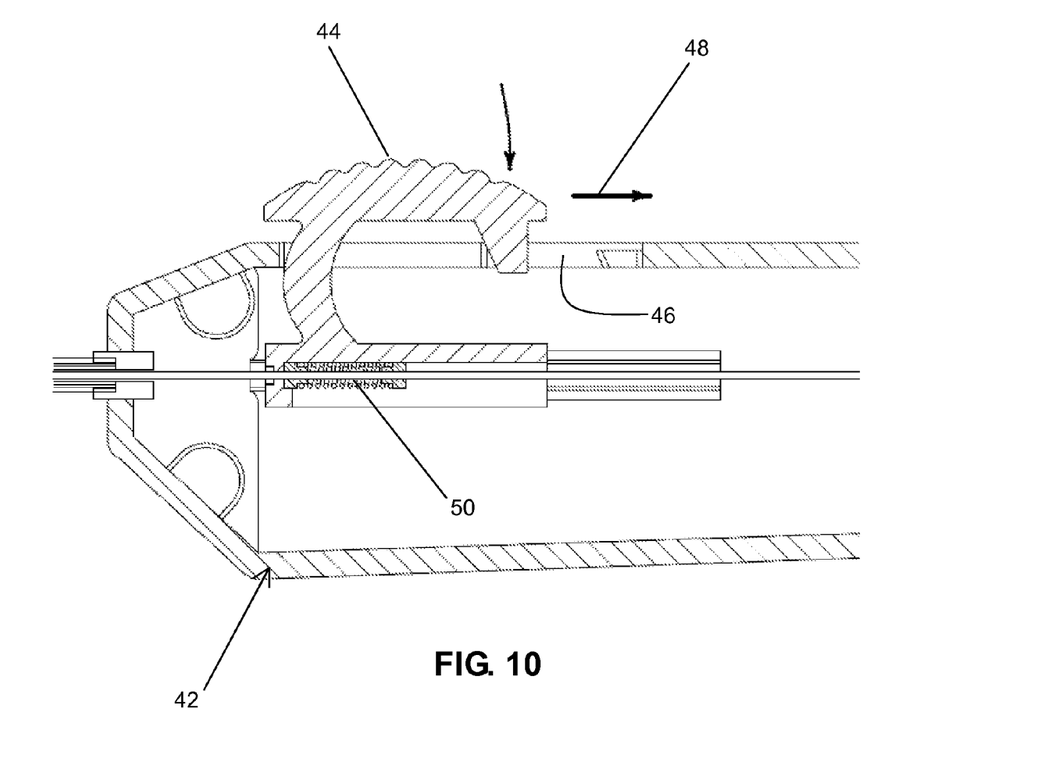
FIG. 10 is a cross-sectional view of a handle portion of the embodiment shown in FIG. 1.

FIG. 10 is a cross-sectional view of a handle portion 42 of the embodiment shown in FIG. 1. This is one possible approach for actuating the extension and retraction of the distal tip 18 relative to the elongate outer tube 12, as discussed above, though many other suitable configurations may be used alternatively. A trigger 44 is slidably disposed on the handle 42, slidable distally through a slot 46 in the direction of arrow 48, and then retractable in the reverse direction. A spring 50 within the handle controls pressure, and a locking mechanism functions to lock the trigger 44 in the retracted state.

Figure 11:
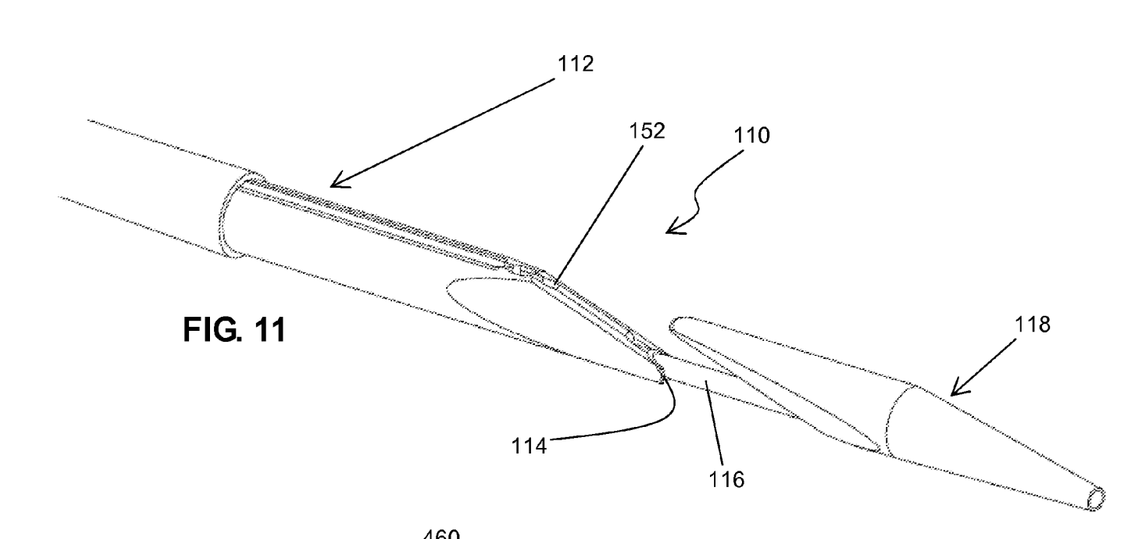
FIG. 11 is an isometric view similar to FIG. 1, illustrating an alternative embodiment of the invention.

Alternative cutting approaches, such as resistive heat (hot wire), ultrasonic, laser, or mechanical approaches, may be used instead of RF energy, if desired. For example, FIG. 11 illustrates an alternative embodiment, wherein a catheter 110 comprises an elongate outer tube 112 having a central lumen 114, a tubular structure 116, and a flexible and tapered distal tip 118. In this embodiment, a single resistive heating wire 152 is used to provide the tissue heating, cutting, and welding function described above. Additionally, an RF configuration applying only monopolar energy, to either the venous or arterial sides, may be employed. A combination of RF energy and resistance heating may also be used. The tip 118, in this embodiment, tracks over the guidewire and dilates the anastomosis site, as in the previous embodiment. The tapered faces of the members 112 and 118 align. The single hot wire 152 down the face cuts a slit in the vessel walls, and the faces are tapered to assist in removing the device.

Now with reference to FIG. 12, a heat spread catheter 210 is illustrated. The catheter 210 comprises a resistive heating element 252, which is employed in a manner similar to that described above in connection with the FIG. 11 embodiment. However, in this embodiment, a conductive material 254 is disposed beneath the heating element 252. In one configuration, this conductive material 254 comprises aluminum, though other conductive bio-compatible materials may also be used. In operation, this conductive material 254 functions to create a heat gradient from the heating element 252, for the purpose of improving the welding function, as described above.

In this embodiment, similar to the foregoing embodiments, the tip 218 tracks over the guidewire and dilates the anastomosis site. The tapered faces of each of the members 212 and 218 align, for clamping the vessel walls. The hot wire 252 is an oval shape and has vertical strips 256 on both sides of the artery. The hot wire cuts an anastomosis larger than the diameter of the shaft 216. Under the hot wire 252, the heat conductive material 254 pulls heat away from the hot wire so that there is a temperature gradient across the face, with the temperature being hottest in the center and cooling as the distance outwardly from the center increases.

The hot wire 252 (heater) is raised above the spreader 254 to increase pressure on the tissue, to thereby assist in the cutting process. Inside the hot wire, there is a cavity to capture the tissue that has been cut. The profile of the distal tip 218 aligns with the edge of the heater when retracted. It is a lower profile than the heat spreader, so that it can be retracted back through the fistula. This also increases the pressure directly on the heater surface to assist in cutting function.

Figures 13, 14:
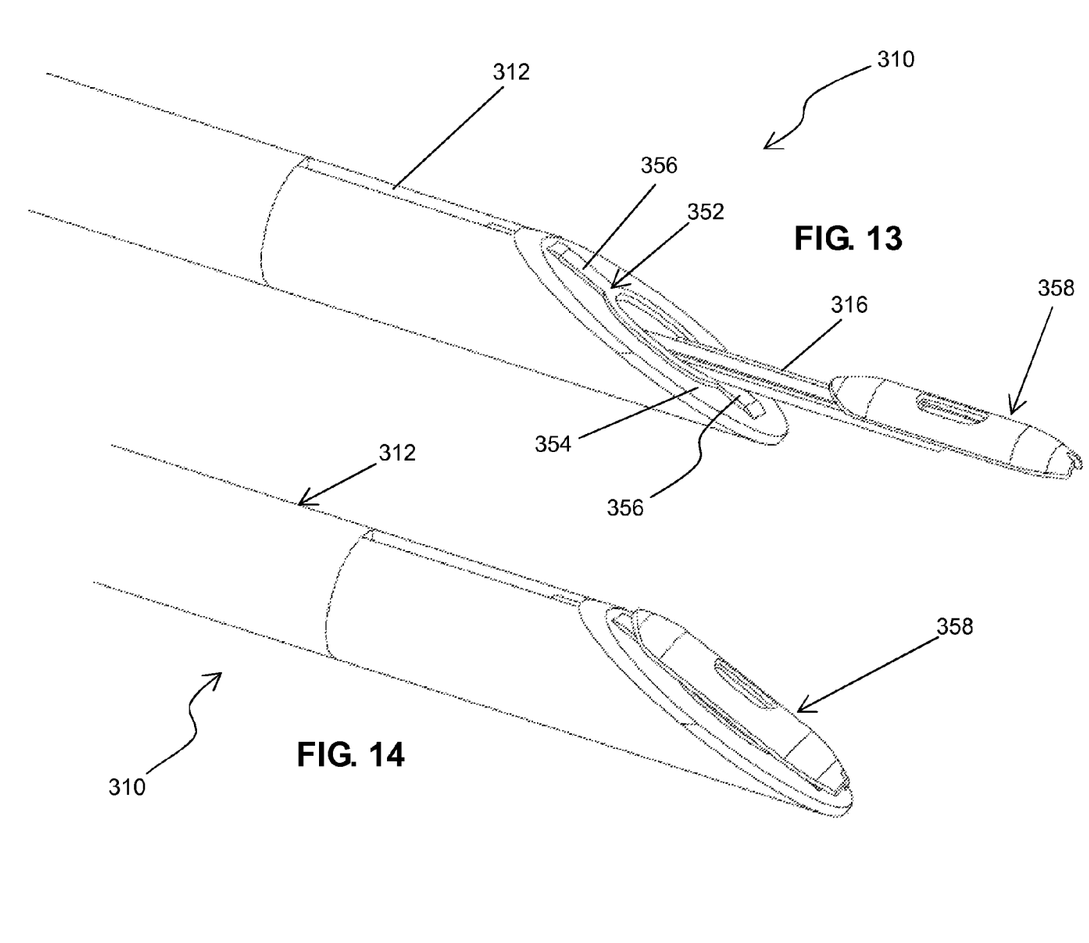
FIG. 13 is an isometric view of still another alternative embodiment of the present invention, wherein a distal toggle member forming part of the device is extended.
FIG. 14 is an isometric view similar to FIG. 13, wherein the distal toggle member is retracted.
Figure 15:
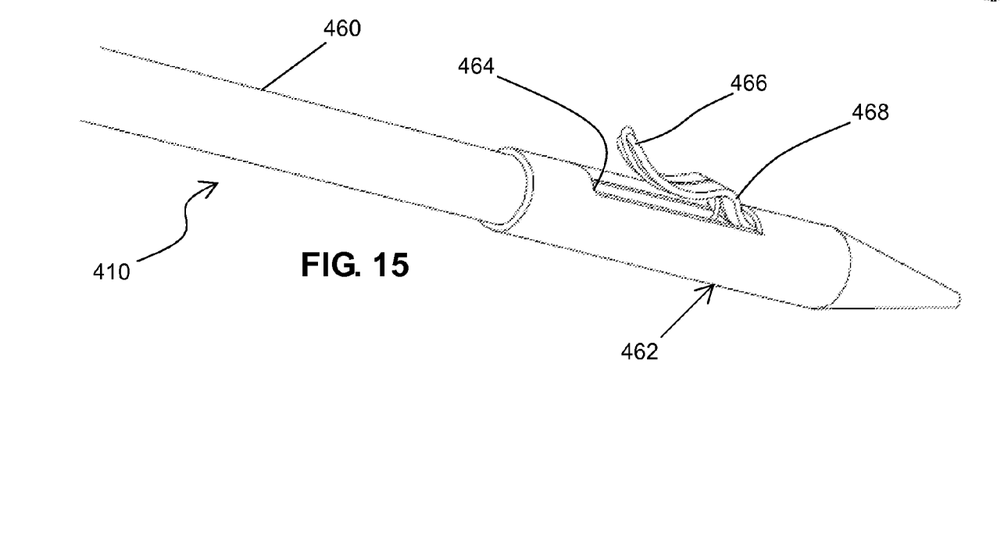
FIG. 15 is an isometric view of yet another alternative embodiment of the present invention.

FIGS. 13 and 14 illustrate still another embodiment 310, comprising a distal toggle member 358. The cutting elements in this embodiment are substantially identical to those shown and described in connection with FIG. 12. As in prior embodiments, the toggle 358 tracks over the guidewire into the artery. When retracted (FIG. 15), the toggle captures the artery and pulls against the vein. The hot wire is an oval shape, has vertical strips 356 on both sides of the artery, and cuts an anastomosis larger than the diameter of the shaft 316. Under the hot wire 352, there is a heat conductive material 356 that pulls heat away from the hot wire so that there is a temperature gradient across the face. The hot wire is raised above the heat spreader to increase pressure on the tissue to help it cut through. Inside the hot wire there is a cavity to capture the tissue that has been cut.

The profile of the toggle 358 aligns with the edge of the heater when retracted. It is of a lower profile than the heat spreader so that it can be retracted back through the fistula. This also increases the pressure directly on the heater surface and helps it cut. Heating elements may also be disposed on the toggle surface to work in conjunction with the heater 352 to cut and weld tissue.

Pivotable toggles and their functionality are discussed in Provisional U.S. Application Ser. No. 61/354,903, filed on Jun. 15, 2010 and already herein expressly incorporated by reference. Those teachings generally apply to this toggle embodiment, regarding the particulars as to how the toggle is used to enter and then retract the second vessel toward the first vessel.

In FIGS. 15-18, there is shown a different cutting approach. In this embodiment, the cutting device 410 comprises a shaft 460 having a distal portion 462. The distal portion comprises a side port 464, from which extends a heater wire 466 which is supported by a flexible clamp 468, preferably fabricated from nitinol or similar material. The heater wire may be resistive or utilise any other energy source as described above.

Figures 16, 17:
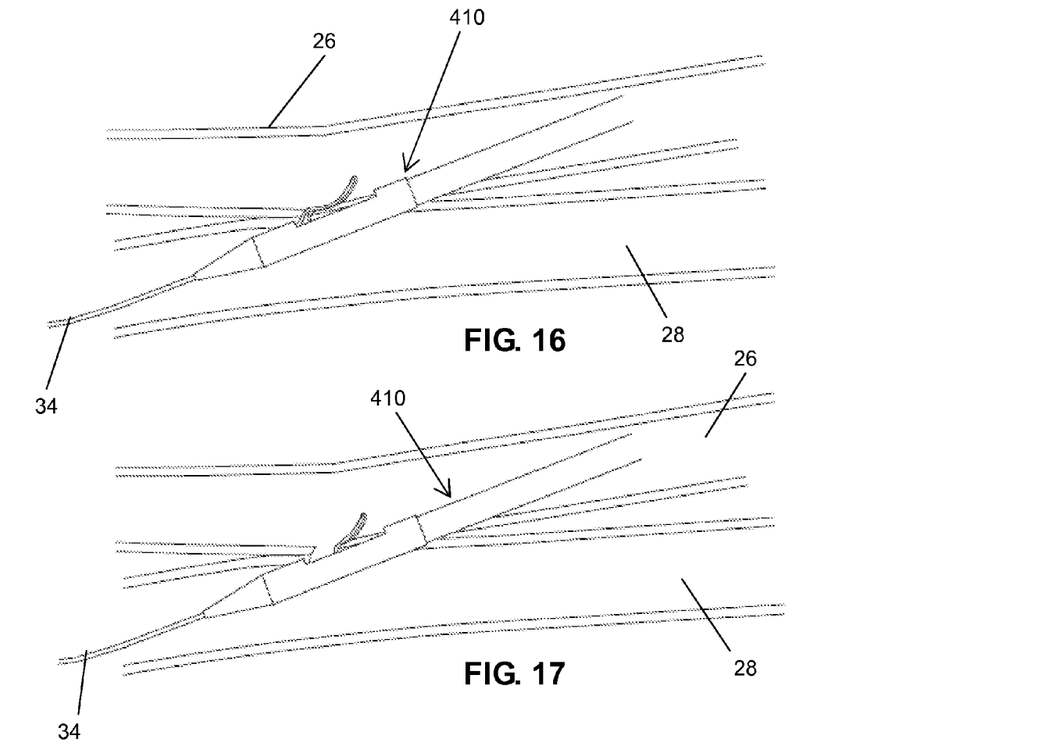
FIGS. 16-18 are schematic sequential views illustrating a method for creating a fistula using the apparatus of FIG. 15.
Figure 18:
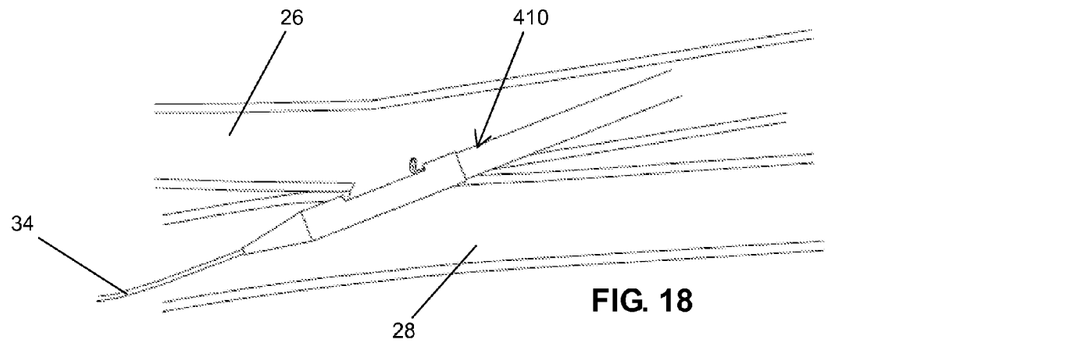

As shown in FIGS. 16-18, access to the anastomosis site is gained by methods as described above and the function of this device, once in place, is to manipulate the wire 466, using the flexible clamp 468 and suitable actuation mechanisms in order to create a fistula of a desired configuration. Specifically, as shown in FIG. 16, the tip 462 tracks over the guidewire 34 and dilates the anastomosis site, as in previously described approaches. The catheter 410 is advanced so that the clip 466 is all the way in the artery 28, and then pulled back to capture the arterial wall under the clip, as illustrated in FIG. 17. The wire is then activated to heat, and then drawn back, which cuts through the arterial and venous walls. The hot wire is then pulled back (FIG. 18), and pulls down the clip portion through the vessel walls.

Accordingly, although an exemplary embodiment and method according to the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A device for creating an arteriovenous (AV) fistula, comprising:
   an elongate member having a distal tapered face, wherein a first outer edge of the distal tapered face is disposed at a more distal location than a second opposed outer edge of the distal tapered face;
   a distal member connected to the elongate member and movable relative to the elongate member, the distal member having a proximal tapered face, the distal tapered face and the proximal tapered face being parallel to and opposed to one another, wherein the distal member is movable between a first configuration in which the distal member is a first distance from the elongate member and a second configuration in which the distal member is a second distance from the elongate member;
   an oval heating member, an entirety of which is disposed around a periphery of, and protruding from, at least one of the proximal tapered face of the distal member or the distal tapered face of the elongate member, at least one strip extending perpendicularly from a portion of the oval heating member;

and a shaft configured to couple the distal member to the elongate member, the shaft being joined to and not extending entirely through the distal member and being extendable, and retractable to move the distal member from the first configuration to the second configuration.

2. The device as recited in claim 1, wherein said elongate member comprises an elongate outer tube.

3. The device as recited in claim 1, wherein said oval heating member is disposed on said proximal tapered face.

4. The device as recited in claim 3, and further comprising a second heating member disposed on said distal tapered face.

5. The device as recited in claim 4, wherein at least one of said oval heating member or said second heating member comprises an energized heater and a heat spreader disposed beneath the energized heater to spread heat away from the energized heater and create a temperature gradient.

6. The device as recited in claim 5, wherein said heat spreader comprises heat conductive material, and is disposed beneath the at least one of said oval heating member or said second heating member.

7. The device as recited in claim 1, wherein said distal member is tapered and flexible.

8. The device as recited in claim 1, wherein said distal member comprises a toggle member which is pivotable relative to said elongate member.

9. The device as recited in claim 8, wherein the toggle member is pivotally connected to said shaft.

10. The device as recited in claim 1, wherein said oval heating member is disposed on said distal tapered face of said elongate member.

11. The device as recited in claim 10, wherein said oval heating member comprises an energized heater and a heat spreader disposed beneath the energized heater to spread heat away from the energized heater and create a temperature gradient.

12. The device as recited in claim 11, wherein said heat spreader comprises heat conductive material.

13. A device for creating an arteriovenous (AV) fistula, comprising: an elongate member having an elliptical, planar distal face, the elliptical, planar distal face disposed at an angle greater than ninety (90) degrees relative to an axis of the elongate member;

a distal member connected to the elongate member, the distal member having an elliptical, planar proximal face, the elliptical, planar distal face and the elliptical, planar proximal face being parallel to and opposed to one another, the elliptical, planar proximal face defining an opening, the elliptical, planar distal face having a lateral dimension greater than a diameter of the opening, one of the elongate member or distal member being movable axially relative to another of the elongate member or distal member between a first configuration and a second configuration;

an oval heating member disposed on and protruding from at least one of the elliptical, planar proximal face of the distal member or the elliptical, planar distal face of the elongate member, at least one strip extending perpendicularly from a portion of the oval heating member;

wherein the heating member is adapted to cut through tissue to create the AV fistula.

14. The device as recited in claim 13, and further comprising a shaft connecting the distal member to the elongate member, the shaft being joined to and not extending entirely through the distal member and being movable within the opening to move the distal member relative to the elongate member between the first configuration and the second configuration.

15. The device as recited in claim 13, wherein said oval heating member is disposed on said elliptical, planar proximal face.

16. The device as recited in claim 15, and further comprising a second heating member disposed on said elliptical, planar distal face.

17. The device as recited in claim 16, wherein at least one of said oval heating member or said second heating member comprises an energized heater and a heat spreader disposed beneath the energized heater to spread heat away from the energized heater and create a temperature gradient.

18. The device as recited in claim 17, wherein said heat spreader comprises heat conductive material, and is disposed beneath the at least one of said oval heating member or said second heating member.

19. The device as recited in claim 13, wherein said oval heating member is disposed on said elliptical, planar distal face of said elongate member.

20. The device as recited in claim 19, wherein said oval heating member comprises an energized heater and a heat spreader disposed beneath the energized heater to spread heat away from the energized heater and create a temperature gradient.

21. The device as recited in claim 1, wherein each of the distal tapered face and the proximal tapered face are non-inflatable and non-deflatable.

22. The device as recited in claim 21, wherein each of the elliptical, planar distal face and the elliptical, planar proximal face are non-inflatable and non-deflatable.

* * * * *